US010328667B2

(12) United States Patent
Yanashima et al.

(10) Patent No.: US 10,328,667 B2
(45) Date of Patent: Jun. 25, 2019

(54) METHOD FOR MANUFACTURING STRETCHABLE SHEET

(75) Inventors: Takuo Yanashima, Utsunomiya (JP); Akio Morita, Ichikai-machi (JP); Makoto Kokubo, Yaita (JP); Kenji Ando, Mashiko-machi (JP)

(73) Assignee: KAO CORPORATION, Tokyo (JP)

( * ) Notice: Subject to any disclaimer, the term of this patent is extended or adjusted under 35 U.S.C. 154(b) by 598 days.

(21) Appl. No.: 13/824,815

(22) PCT Filed: Oct. 18, 2011

(86) PCT No.: PCT/JP2011/073931
§ 371 (c)(1),
(2), (4) Date: Mar. 18, 2013

(87) PCT Pub. No.: WO2012/056942
PCT Pub. Date: May 3, 2012

(65) Prior Publication Data
US 2013/0178349 A1    Jul. 11, 2013

(30) Foreign Application Priority Data

Oct. 28, 2010    (JP) .................. 2010-241694

(51) Int. Cl.
*B32B 5/26*    (2006.01)
*A61F 13/15*    (2006.01)
*A61F 13/49*    (2006.01)

(52) U.S. Cl.
CPC .......... *B32B 5/26* (2013.01); *A61F 13/15601* (2013.01); *A61F 13/15609* (2013.01); *A61F 13/49014* (2013.01)

(58) Field of Classification Search
CPC .......... A61F 13/15577; A61F 13/15593; A61F 13/4902; A61F 13/15; B32B 5/26;
(Continued)

(56) References Cited

U.S. PATENT DOCUMENTS 4,776,911 A * 10/1988 Uda ................. A41D 27/00
156/161
4,789,107 A * 12/1988 Hauser ............. B65H 54/42
242/413.7
(Continued)

FOREIGN PATENT DOCUMENTS

CN    101553611 A    10/2009
CN    101557929 A    10/2009
(Continued)

OTHER PUBLICATIONS

International Search Report issued in PCT/JP2011/073931, dated Jan. 24, 2012.
(Continued)

*Primary Examiner* — Andrew M Tecco
*Assistant Examiner* — Mary C Hibbert
(74) *Attorney, Agent, or Firm* — Birch, Stewart, Kolasch & Birch, LLP

(57) ABSTRACT

The present invention provides a method for continuously manufacturing a stretchable sheet (3) with a thread-shaped elastic body (7) fixed between a pair of belt-shaped sheets (50, 60) in a stretched state, the method including a supply process of introducing the fed thread-shaped elastic body (7) to elastic body winding means (14) in a stretched state, a conveyance process of continuously winding the thread-shaped elastic body (7) to a thread-conveying longitudinal structure (12, 13) using the elastic body winding means (14) and conveying the wound thread-shaped elastic body in a longitudinal direction of the structure (12, 14), and an integration process of fixing the thread-shaped elastic body (7) as sandwiching between the sheets (50, 60). In the supply process, the thread-shaped elastic body (7) is introduced to the elastic body winding means (14) while adjusting a speed of the thread-shaped elastic body (7) to be equal to or higher than a winding speed against the pair of conveying belts (12, (Continued)

13) with speed adjusting means (15B) which is arranged at the upstream side of the elastic body winding means (14).

3 Claims, 4 Drawing Sheets

(58) Field of Classification Search
CPC .. B32B 7/14; B32B 37/14; B32B 5/00; B32B 38/00; B65H 81/00; B65H 59/00
USPC ........ 493/379; 156/160, 179, 439, 164, 495; 604/391, 378; 428/219
See application file for complete search history.

(56) References Cited

U.S. PATENT DOCUMENTS

| | | | |
|---|---|---|---|
| 5,004,466 A | 4/1991 | Uda et al. | |
| 5,643,396 A | 7/1997 | Rajala et al. | |
| 6,808,582 B2 * | 10/2004 | Popp | A61F 13/15609 156/160 |
| 7,361,246 B2 * | 4/2008 | Chang | A61F 13/15593 156/177 |
| 2008/0132136 A1 | 6/2008 | Uematsu et al. | |
| 2009/0306617 A1 | 12/2009 | Tsang et al. | |
| 2010/0075103 A1 | 3/2010 | Miyamoto | |
| 2010/0112313 A1 | 5/2010 | Nakakado | |
| 2010/0262109 A1 | 10/2010 | Eriksson | |

FOREIGN PATENT DOCUMENTS

| | | |
|---|---|---|
| CN | 101854898 A | 10/2010 |
| EP | 2 438 892 A1 | 4/2012 |
| JP | 63-243309 A | 10/1988 |
| JP | 2001-346825 A | 12/2001 |
| JP | 2005-67791 A | 3/2005 |
| JP | 2005-320636 A | 11/2005 |
| JP | 2010-022549 A | 2/2010 |
| JP | 2010-22550 A | 2/2010 |
| JP | 2010-22588 A | 2/2010 |
| JP | 2011-127240 A | 6/2011 |
| WO | WO 98/55298 A1 | 12/1998 |

OTHER PUBLICATIONS

International Preliminary Report on Patentability and Translation of the Written Opinion of the International Searching Authority (Forms PCT/IB/338, PCT/IB/373 and PCT/ISA/237) for International Application No. PCT/JP2011/073931, dated May 23, 2013.
Extended European Search Report, dated Apr. 24, 2017, for European Application No. 11836078.3.

* cited by examiner ance direction of the belt-shaped sheets. The method
METHOD FOR MANUFACTURING STRETCHABLE SHEET

TECHNICAL FIELD

The present invention relates to a method for manufacturing a stretchable sheet.

BACKGROUND ART

From viewpoints of being eco-friendly and reducing cost while suppressing materials and waste to the extent possible, there has been known an open-style type disposable diaper which is manufactured by attaching a waist panel material to a rectangular absorbent body including an absorbent member while previously manufacturing the waist panel material having a fastening tape in a separate process. From a viewpoint of fit, it is preferable that the waist panel material is a stretchable member. Generally, the waist panel material is formed by utilizing a stretchable film. However, since a stretchable sheet is expensive, it is preferable to form the waist panel material by utilizing a so-called thread rubber which is a general elastic member. Here, in a case that a process to obtain a waist panel material using thread rubber and a process to obtain an open-style type disposable diaper as attaching the waist panel material to the absorbent body are continuously performed in sequence, a stretchable direction of the waist panel material formed by using the thread rubber generally becomes the same as the conveyance direction of the absorbent body to be a direction perpendicular to a stretchable direction of the waist panel material required for wearing an open-style type disposable diaper. Accordingly, in a case of manufacturing an open-style type disposable diaper by attaching the waist panel material formed by using thread rubber to the absorbent body in an inline process, the waist panel material formed by using thread rubber is required to be attached to the absorbent body after being rotated by 90°. Since an apparatus to rotate the waist panel material by 90° is required separately, equipment investment is increased.

As a method without using an apparatus to cause rotation of 90° as described above, for example, Patent Literature 1 and Patent Literature 2 disclose a stretchable sheet manufacturing method including a process of bonding a thread-shaped elastic body to a sheet in a state of being stretched while adhesive is applied to a permeable sheet moving in a length direction and the thread-shaped elastic body provided with tension is translated onto the adhesive applied face along the sheet face of the moving sheet toward the sheet moving direction in a zigzag state and a process of cutting the thread-shaped elastic body at both ends. Further, Patent Literature 1 also discloses a method to rearrange the zigzag thread-shaped elastic body to be parallel.

However, being different from a case of fixing the thread-shaped elastic body introduced along the sheet conveyance direction to the sheet, with the method to obtain a stretchable sheet by orienting the thread-shaped elastic body in a direction intersecting with the sheet conveyance direction as being wound around a pair of feeding belts and integrating the thread-shaped elastic body in the abovementioned state with the sheet as disclosed in Patent Literatures 1 and 2, stretch stress characteristics of sheets are more likely to be fluctuated in accordance with a manufacturing speed of stretchable sheets. For example, when the manufacturing speed becomes high, it becomes difficult to maintain stretch stress characteristics of manufactured sheets to be constant.

CITATION LIST

Patent Literature

Patent Literature 1: JP 63-243309 A
Patent Literature 2: JP 2010-22588 A

SUMMARY OF INVENTION

The present invention relates to a method for manufacturing stretchable sheet which is capable of resolving the abovementioned drawbacks in the related art.

The present invention provides a method for continuously manufacturing a stretchable sheet with a thread-shaped elastic body fixed between a pair of belt-shaped sheets in a state of being stretched in a direction intersecting with a conveyance direction of the belt-shaped sheets. The method of the present invention includes a supply process of continuously leading out the thread-shaped elastic body and introducing the fed thread-shaped elastic body to elastic body winding means, a conveyance process of continuously winding the thread-shaped elastic body to a thread-conveying longitudinal structure using the elastic body winding means and conveying the wound thread-shaped elastic body in a longitudinal direction of the thread-conveying longitudinal structure, and an integration process of fixing the conveyed thread-shaped elastic body as sandwiching between the sheets. In the supply process, the thread-shaped elastic body is introduced to the elastic body winding means while adjusting a speed of the thread-shaped elastic body to be equal to or higher than a winding speed to the thread-conveying longitudinal structure with speed adjusting means which is arranged at the upstream side of the elastic body winding means.

DESCRIPTION OF EMBODIMENTS

In the following, a method for manufacturing stretchable sheet of the present invention will be described based on a preferable embodiment thereof with reference to the drawings.

Figure 1:
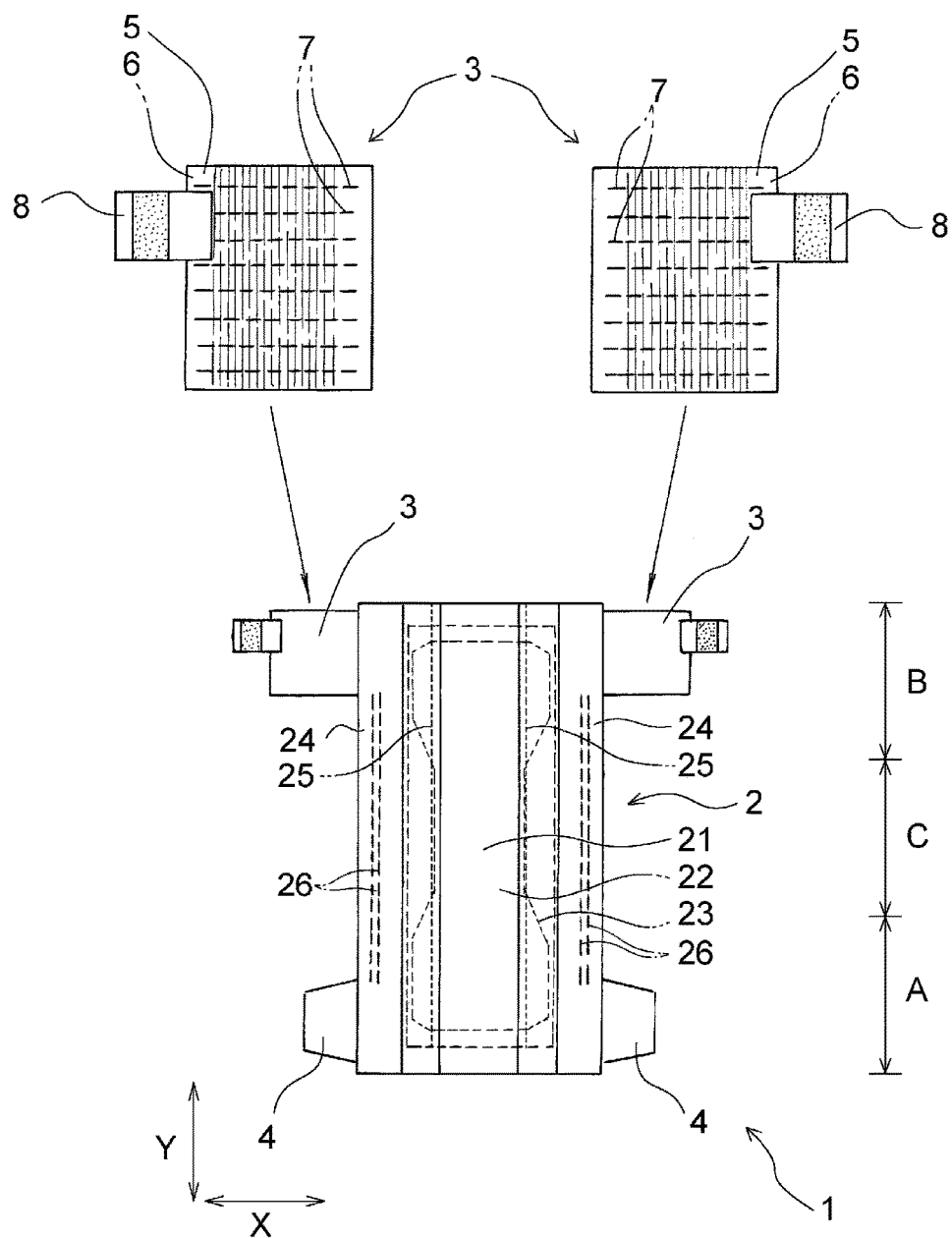
FIG. 1 is a plane view illustrating a waist panel material and an open-style type disposable diaper obtained in an embodiment of the present invention.

As illustrated in FIG. 1, the stretchable sheet manufactured in the present embodiment is used as a waist panel 3 of an open-style type disposable diaper 1, for example. Here, description is firstly performed on the open-style type disposable diaper 1 in which a stretchable sheet manufactured in the present embodiment is used for a waist panel.

As illustrated in FIG. 1, the open-style type disposable diaper 1 (hereinafter, called the "diaper 1" as well) includes an absorbent body 2 which has a front section A adapted to be worn about the front of a wearer, a rear section B adapted to be worn about the back of a wearer and a crotch section C adapted to be worn between the front section A and the rear section B, and a right-left pair of waist panels 3, 3 continuously arranged outward to the right and left of the rear section B. As illustrated in FIG. 1, the diaper 1 includes a right-left pair of panel members 4, 4 continuously arranged outward to the right and left of the front section A. Here, as illustrated in FIG. 1, the absorbent body 2 of the diaper 1 is rectangular in a state of being planarly-expanded. Further, as illustrated in FIG. 1, the panel member 4 of the diaper 1 is trapezoidal in a state of being planarly-expanded, and is fixed at the lower base side thereof having a larger length to the absorbent body 2 with means such as adhesive and fusion.

In the following, description is performed as the longitudinal direction of the absorbent body 2 (the longitudinal direction of the diaper 1 as well) being denoted by a Y-direction and the width direction of the absorbent body 2 (the width direction of the diaper 1 as well) being denoted by an X-direction.

The pair of waist panels 3, 3 is rectangular respectively in a state of being planarly-expanded. Each waist panel 3 includes two sheets 5, 6 and a plurality of thread-shaped elastic body 7 arranged between the two sheets 5, 6 in a stretched state. Each waist panel 3 is structured with a stretchable sheet which is fixed in a state that the thread-shaped elastic body 7 is stretched between the pair of sheets 5, 6 in a direction intersecting with the Y-direction. Specifically, as illustrated in FIG. 1, each waist panel 3 is formed by arranging thread-shaped elastic bodies between the two rectangular sheets 5, 6 having the same shape and size as being stretched in a direction (X-direction) intersecting with the Y-direction at approximately regular intervals in the Y-direction and integrally fixed to the thread-shaped elastic bodies with means such as adhesive and fusion. A fastening tape 8 is fixed to an outer end part in the X-direction of each rectangular waist panel 3 formed as described above with means such as adhesive and fusion. Further, each rectangular waist panel 3 is fixed at an inner end part in the X-direction to the rear section B of the absorbent body 2 with means such as adhesive and fusion and extends outward in the X-direction from the rear section B. Here, although being stretched in a direction perpendicular to the Y-direction, the thread-shaped elastic bodies provided to the waist panel 3 (stretchable sheet) manufactured in the present embodiment are only required to be stretched in a direction intersecting with the Y-direction.

As illustrated in FIG. 1, the absorbent body 2 is provided with a liquid permeable topsheet 21, a liquid impermeable or water-repellant backsheet 22, and a liquid-retainable absorbent member 23 interposed between both the sheets 21, 22. As illustrated in FIG. 1, the absorbent body 2 is formed by joining the topsheet 21 forming an inner face of the diaper 1 and the backsheet 22 forming an outer face of the diaper 1 in the state that the absorbent member 23 is interposed between both the sheets 21, 22. Further, as illustrated in FIG. 1, the absorbent body 2 has standing-guard forming sheets 24, 24 arranged along both side parts thereof in the Y-direction. The standing-guard forming sheets 24 are fixed to the topsheet 21 along the both side parts in the Y-direction of the absorbent body 2. Each standing-guard forming sheet 24 includes an elastic member 25 for forming a standing-guard along an inner vicinity of an end edge thereof in the X-direction, so that a standing guard is formed with a portion having a predetermined width from the end edge separated from the topsheet 21 owing to contraction force of the elastic member 25 while worn. Further, elastic members 26 for forming leg gathers are arranged at both side parts of the absorbent body 2 in the longitudinal direction which are located at leg circumference of wearer while worn. Leg gathers are formed owing to contraction of the elastic members 26 while worn and excellent fit around legs can be obtained.

Materials for forming the diaper 1 will be described.

The sheets 5, 6 and the panel member 4 which structure the waist panel 3 may adopt anything normally used for an absorbent article such as a disposable diaper without specific limitations. For example, the sheets 5, 6 and the panel member 4 may adopt nonwoven, woven, a film, a laminated sheet thereof, or the like. The topsheet 21 and the backsheet 22 which structure the absorbent body 2 may adopt anything normally used for an absorbent article such as a disposable diaper respectively without specific limitations. For example, the topsheet 21 may adopt nonwoven or the like being hydrophilic and liquid permeable. The backsheet 22 may adopt a resin film being liquid impermeable or water-repellant, a laminated body of the resin film and nonwoven, or the like. The absorbent member 23 may adopt an absorbent core being an aggregation of fibers such as pulp fibers (may be nonwoven) or an aggregation at which absorbent polymer particles are retained as being covered with a core wrap sheet formed of permeable thin paper or nonwoven or the like. The standing-guard forming sheet 24 structuring the standing-guard may adopt a stretchable sheet, nonwoven, woven, a laminated sheet thereof, or the like.

The thread-shaped elastic body 7 and the elastic member 25 structuring the standing-guard may adopt a thread-shaped stretchable material formed of natural rubber, polyurethane, polystyrene-polyisoprene copolymer, polystyrene-polybutadiene copolymer, polyethylene-α-olefin copolymer such as ethyl-acrylate-ethylene, or the like. The thread-shaped elastic body in the present invention may have a cross-section being like a narrow belt shape of an oval, a rectangle or the like in addition to a circle or a square and may adopt a multifilament type. A width (or diameter) of the thread-shaped elastic body is in a range of 0.1 to 3 mm for example, and is preferably 1 mm or less. For example, the fastening tape 8 may be formed by sticking a hook member of a mechanical fastener on one face of a tape base material such as nonwoven with thermal fusion, adhesive or the like.

Next, a preferable embodiment of a method for manufacturing stretchable sheet of the present invention will be described with reference to the drawings as exemplifying a case of manufacturing the abovementioned waist panel 3 (stretchable sheet) of the diaper 1.

Figure 2:
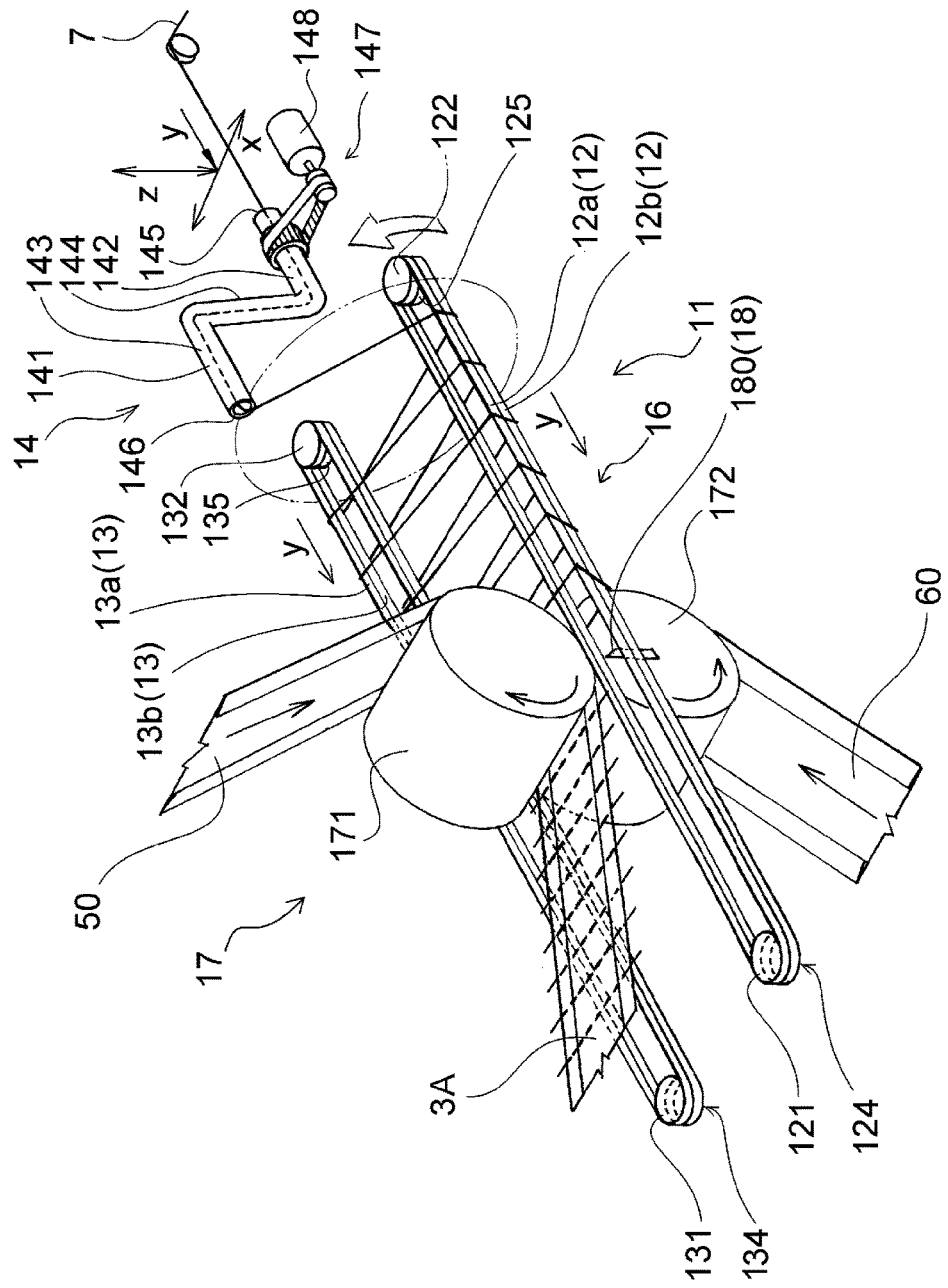
FIG. 2 is a perspective view illustrating a stretchable sheet manufacturing apparatus preferably used for performing the manufacturing method of an embodiment of the present invention.

FIG. 2 schematically illustrates a manufacturing apparatus preferably used for a method of manufacturing the waist panel 3 (stretchable sheet) of the present embodiment.

Figure 3:
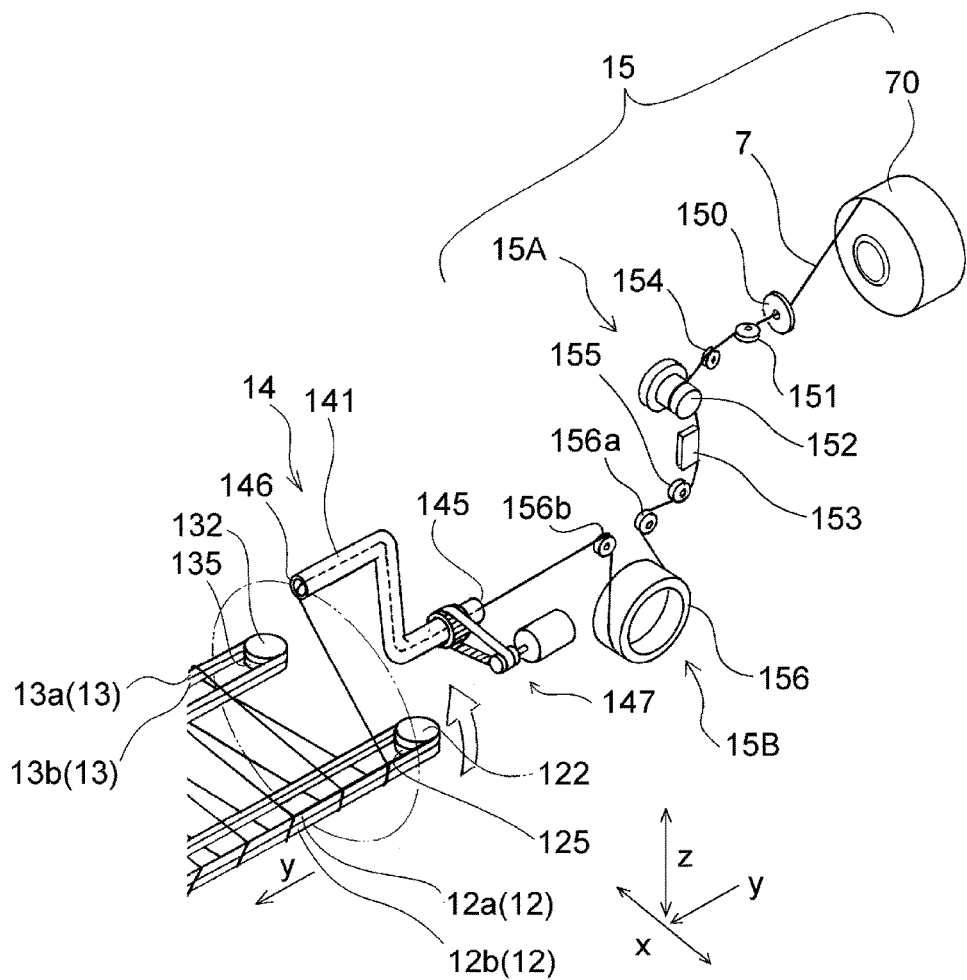
FIG. 3 is a perspective view illustrating a structure of the upstream side from a rotary arm (elastic body winding means) of the apparatus illustrated in FIG. 2.

As illustrated in FIG. 2, a manufacturing apparatus 11 is an apparatus to continuously manufacture a stretchable sheet 3A which is used for the waist panel 3 and is provided with a pair of conveying belts 12, 13 separated in a direction (x-direction) being perpendicular to a sheet conveyance direction (y-direction), and a rotary arm (elastic body winding means) 14 for winding an elastic body to continuously wind the thread-shaped elastic body 7. Further, as illustrated in FIGS. 2 and 3, the manufacturing apparatus 11 is provided with elastic body supply means 15 which continuously unreels the thread-shaped elastic body 7 and introduces the thread-shaped elastic body 7 to the rotary arm 14 in a stretched state, conveying means 16 which conveys the thread-shaped elastic body 7 with the pair of conveying belts 12, 13 between a pair of belt-shaped sheets 50, 60, integrating means 17 which fixes the thread-shaped elastic body 7 in a stretched state between the pair of belt-shaped sheets 50, 60 with a pair of nip rollers 171, 172, and cutting means 18 which cuts the thread-shaped elastic body 7 which is extended from both end parts in the width direction of the belt-shaped sheets 50, 60.

In the present embodiment, the pair of conveying belts 12, 13 is a thread-conveying longitudinal structure in the present invention and the longitudinal direction of the thread-conveying longitudinal structure is an extended direction (y-direction) of both the conveying belts 12, 13.

A sheet conveyance direction is a conveyance direction of the thread-shaped elastic body 7 wound around the pair of conveying belts 12, 13 or a conveyance direction of the sheets (belt-shaped sheets 50 and/or 60) integrated with the thread-shaped elastic body 7.

In FIG. 2, the y-direction indicated by arrows denotes the conveyance direction of the thread-shaped elastic body 7 and the pair of belt-shaped sheets 50, 60 being the sheet conveyance direction also as being the same direction as the conveyance direction of the waist panel 3 (stretchable sheet) eventually manufactured in the present embodiment and the conveyance direction of a continuous member of the diaper 1 to which the waist panel 3 (stretchable sheet) is attached.

Further, in FIG. 2, the x-direction indicated by an arrow denotes the width direction of the belt-shaped sheets 50, 60 and the direction perpendicular to the sheet conveyance direction. Further, in FIG. 2, a z-direction indicated by an arrow denotes a direction in which the pair of later-mentioned nip rollers 171, 172 are mutually faced.

As illustrated in FIG. 2, the conveying belt 12 of the conveying means 16 is an endless rotary belt which includes an upper conveying belt 12a and a lower conveying belt 12b in a two-tier fashion. The upper conveying belt 12a is routed between pulleys 121, 122 which have a rotation axis direction respectively arranged in the z-direction. The lower conveying belt 12b is routed between pulleys 124, 125 which have a rotation axis direction respectively arranged in the z-direction. The pulley 121 is located at the downstream side of the pair of nip rollers 171, 172 which fixes the stretched thread-shaped elastic body 7 between the pair of belt-shaped sheets 50, 60. The pulley 122 is located at the upstream side of the nip rollers 171, 172. The pulley 124 is located at the downstream side of the nip rollers 171, 172. The pulley 125 is located at the upstream side of the nip rollers 171, 172. The pulleys 121, 124 are arranged at the same position in a two-tier fashion. Further, the pulleys 122, 125 are also arranged at the same position in a two-tier fashion. Further, the pulley 122 (pulley 125) is located outward in the x-direction from end parts in the x-direction of the belt-shaped sheets 50, 60. The pulley 121 and the pulley 124 are provided consecutively with a servomotor (not illustrated) respectively at a drive portion thereof, so that respective rotation speeds of the upper conveying belt 12a and the lower conveying belt 12b can be varied.

Similarly to the conveying belt 12, the conveying belt 13 of the conveying means 16 is an endless rotary belt which includes an upper conveying belt 13a and a lower conveying belt 13b in a two-tier fashion, as illustrated in FIG. 2. The upper conveying belt 13a is routed between pulleys 131, 132 which have a rotation axis direction respectively arranged in the z-direction. The lower conveying belt 13b is routed between pulleys 134, 135 which have a rotation axis direction respectively arranged in the z-direction. The pulley 131 is located at the downstream side of the pair of nip rollers 171, 172. The pulley 132 is located at the upstream side of the nip rollers 171, 172. The pulley 134 is located at the downstream side of the nip rollers 171, 172. The pulley 135 is located at the upstream side of the nip rollers 171, 172. The pulleys 131, 134 are arranged at the same position in a two-tier fashion. Further, the pulleys 132, 135 are also arranged at the same position in a two-tier fashion. Further, the pulley 132 (pulley 135) is located outward in the x-direction from end parts in the x-direction of the belt-shaped sheets 50, 60. The pulleys 131, 134 are provided consecutively with a servomotor (not illustrated) respectively at a drive portion thereof, so that respective rotation speeds of the upper conveying belt 13a and the lower conveying belt 13b can be varied.

As illustrated in FIG. 2, the conveying belt 12 (the upper conveying belt 12a and the lower conveying belt 12b) is arranged from the upstream side to the downstream side of the pair of nip rollers 171, 172 as being routed to the pulleys 121, 122 and the pulleys 124, 125 which are arranged as described above. Further, the conveying belt 13 (the upper conveying belt 13a and the lower conveying belt 13b) is arranged from the upstream side to the downstream side of the pair of nip rollers 171, 172 as being routed to the pulleys 131, 132 and the pulleys 134, 135 which are arranged as described above. Further, the conveying belt 12 (the upper conveying belt 12a and the lower conveying belt 12b) and the conveying belt 13 (the upper conveying belt 13a and the lower conveying belt 13b) are located outward in the x-direction of the belt-shaped sheets 50, 60 as being bilaterally symmetric to each other. The conveying belt 12 (the upper conveying belt 12a and the lower conveying belt 12b) and the conveying belt 13 (the upper conveying belt 13a and the lower conveying belt 13b) are rotated so that each outer circumferential side thereof is moved in the y-direction.

It is preferable that all the conveying belt 12 (the upper conveying belt 12a and the lower conveying belt 12b) and the conveying belt 13 (the upper conveying belt 13a and the lower conveying belt 13b) are timing belts. A control unit (not illustrated) provided to the manufacturing apparatus 11 controls rotation speeds of the conveying belt 12 (the upper conveying belt 12a and the lower conveying belt 12b) and the conveying belt 13 (the upper conveying belt 13a and the lower conveying belt 13b), that is, rotation speeds of servomotors (not illustrated) arranged respectively at the drive portions of the pulley 121, the pulley 124, the pulley 131, and the pulley 134.

As illustrated in FIG. 2, the rotary arm 14 is provided with an arm portion 141 including a shaft portion 142, an orbiting portion 143 and a connection portion 144, and a drive mechanism 147 which rotates the arm portion 141 with a center line of the shaft portion 142 as a rotation axis. The connection portion 144 is connected respectively to the shaft portion 142 and the orbiting portion 143 as being angled therewith. The orbiting portion 143 and the shaft portion 142 are approximately in parallel. The shaft portion 142 includes an inlet port 145 for the thread-shaped elastic body 7 at one end thereof. The orbiting portion 143 includes an outlet port 146 for the thread-shaped elastic body 7 at one end thereof. The thread-shaped elastic body 7 led in from the inlet port 145 is smoothly led out from the outlet port 146 as passing through the shaft portion 142, the connection portion 144, and the orbiting portion 143. It is also possible to arrange a variety of known members (a driven roll, a low-friction member or the like) which can reduce friction against the thread-shaped elastic body 7 at a bent part of the arm portion 141, the outlet port 146 and the like.

In the orbiting portion 143, the outlet port 146 is arranged at a position being at the downstream side from an end part of the upstream side of the conveying belt 12 (the upper conveying belt 12*a* and the lower conveying belt 12*b*) and the conveying belt 13 (the upper conveying belt 13*a* and the lower conveying belt 13*b*). In the rotary arm 14, a servomotor 148 is attached to the drive portion (shaft portion 142). Rotation of the servomotor 148 causes the orbiting portion 143 to orbit on outer periphery of the conveying belt 12 (the upper conveying belt 12*a* and the lower conveying belt 12*b*) and the conveying belt 13 (the upper conveying belt 13*a* and the lower conveying belt 13*b*). A diameter of an orbit on which the outlet port 146 is rotated is larger than a distance between outer faces of the pair of conveying belts 12, 13.

Owing to the rotary arm 14 as described above, the introduced thread-shaped elastic body 7 can be continuously wound to the outer periphery sides at end parts of the upstream side of the conveying belt 12 (the upper conveying belt 12*a* and the lower conveying belt 12*b*) and the conveying belt 13 (the upper conveying belt 13*a* and the lower conveying belt 13*b*). A rotation speed of the rotary arm 14, that is, a rotation speed of the servomotor 148 is controlled by the control unit (not illustrated) provided to the manufacturing apparatus 11.

As illustrated in FIG. 3, the elastic body supply means 15 is provided with means to unreel the thread-shaped elastic body 7 from a bobbin 70, tension adjusting means 15A which applies predetermined tension to the thread-shaped elastic body 7 unreeled from the bobbin 70, and speed adjusting means 15B which is located at the downstream side of the tension adjusting means 15A and which adjusts a speed of the thread-shaped elastic body 7 fed from the tension adjusting means 15A for introducing to the rotary arm (elastic body winding means) 14.

The tension adjusting means 15A includes a tensor 151 which is located at the downstream side of the bobbin 70 and which applies tension to the thread-shaped elastic body 7 with braking, a take-off roller 152 which is located at the downstream side of the tensor 151, and a tension measuring unit 153 which is located at the downstream side of the take-off roller 152. The take-off roller 152 has a rotation axis direction arranged in the x-direction. A servomotor (not illustrated) is attached to a drive portion of the take-off roller 152. The take-off roller 152 is used with the thread-shaped elastic body 7 wound to the outer circumference thereof in one turn or a plurality of turns (preferably, two turns). The take-off roller 152 used in the present embodiment also serves as the whole or a part of the unreeling means. The thread-shaped elastic body 7 unreeled from the bobbin 70 is introduced to the tensor 151 through a guide hole of a guide member 150 by the take-off roller 152.

In the tension adjusting means 15A, tension of the thread-shaped elastic body 7 between the take-off roller 152 and the guide roller 155 is detected by the tension measuring unit 153 and feedback control of the rotation speed of the take-off roller 152 is performed based on a detection output from the tension measuring unit 153 by the control unit (not illustrated) provided to the manufacturing apparatus 11. With the above, tension of the thread-shaped elastic body 7 fed from the guide roller 155 can be adjusted to predetermined tension.

Speed adjusting means 15B adjusts a speed of the thread-shaped elastic body 7 fed from the tension adjusting means 15A and introduces the speed-adjusted thread-shaped elastic body 7 to the rotary arm (elastic body winding means) 14. As illustrated in FIG. 3, the speed adjusting means 15B includes a feed roller 156 at a vicinity of the rotary arm 14. The feed roller 156 is arranged between the rotary arm 14 and the take-off roller 152 with a rotation axis direction thereof arranged in the x-direction. Guide rollers 156*a*, 156*b* are arranged before and after the feed roller 156. A servomotor (not illustrated) is attached to a drive portion of the feed roller 156. Rotation speed of the servomotor (not illustrated), that is, rotation speed of the feed roller 156, is controlled by the control unit (not illustrated) provided to the manufacturing apparatus 11.

It is preferable that the feed roller 156 is arranged at a vicinity of the rotary arm 14, especially, immediately before the rotary arm 14 in a conveyance passage of the thread-shaped elastic body. For example, it is preferable that a length of the conveyance passage of the thread-shaped elastic body after leaving from the feed roller 156 until being introduced to the rotary arm 14 is preferably in a rage of 10% to 50% and more preferably in a range of 10% to 30% against the total length of the conveyance passage of the thread-shaped elastic body from the bobbin 70 to the rotary arm 14.

Figure 4:
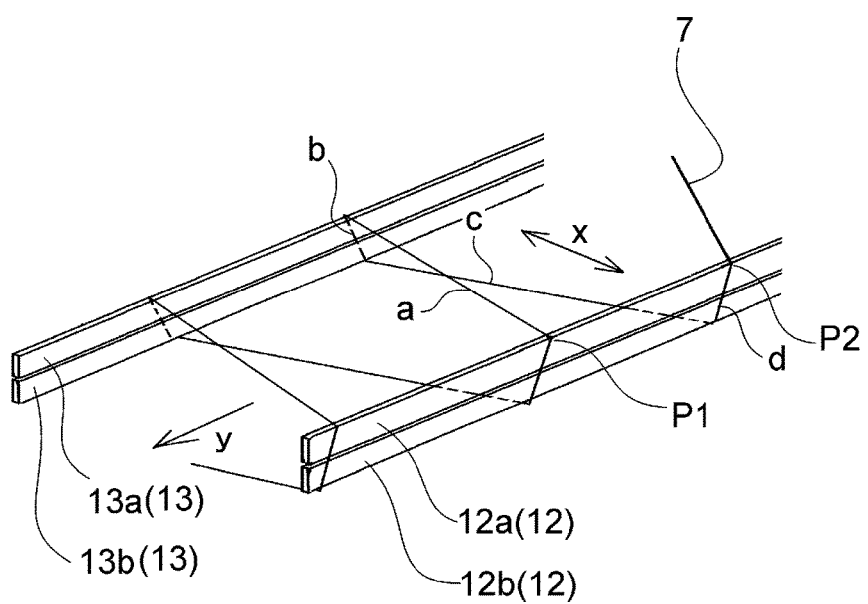
FIG. 4 is an explanatory view for explaining a winding speed.

As illustrated in FIGS. 2 and 4, the integrating means 17 includes the pair of nip rollers 171, 172. The pair of nip rollers 171, 172 may adopt a cylindrical roller made of metal or a cylindrical roller made of low hardness silicon-rubber. A servomotor (not illustrated) is attached to a drive portion for either of the pair of nip rollers 171, 172 and a rotation speed thereof is controlled by the control unit (not illustrated) provided to the manufacturing apparatus 11. The pair of nip rollers 171, 172 is provided with a gear for drive transmission respectively at each rotation axis. The drive means (not illustrated) can control a rotation speed of the servomotor (not illustrated), that is, a rotation speed of one of the nip rollers 171, 172 based on a manufacturing speed of stretchable sheets. At that time, owing to engagement of the gears for drive transmission, drive force is transmitted to the other of the nip rollers 171, 172 as well, so that the pair of nip rollers 171, 172 can be rotated. Bearing sections of the pair of nip rollers 171, 172 are pressurized respectively by utilizing force of hydraulic pressure, air pressure, a spring or the like for reliably fixing the stretched thread-shaped elastic body between the pair of belt-shaped sheets 50, 60.

As illustrated in FIG. 2, the pair of nip rollers 171, 172 is located between the inner circumferential side of the conveying belt 12 (the upper conveying belt 12*a* and the lower conveying belt 12*b*) and the inner circumferential side of the conveying belt 13 (the upper conveying belt 13*a* and the lower conveying belt 13*b*).

As illustrated in FIG. 2, the cutting means 18 include cutters 180 respectively with a sharp cutting blade at a portion to which the conveyed thread-shaped elastic body 7 is abutted (the cutter 180 at the conveying belt 13 side is, not illustrated in the drawing). The cutter 180 is arranged at a position to be abutted to the thread-shaped elastic body 7 with a support body (not illustrated). The thread-shaped elastic body 7 is cut by being pressed to the cutter 180 as being conveyed by the conveying belts 12, 13. In the y-direction, the cutting means 18 is located between the pair of nip rollers 171, 172 and the pulleys 121, 124 of the conveying belt 12 (the upper conveying belt 12*a* and the lower conveying belt 12*b*) and the pulleys 131, 134 of the conveying belt 13 (the upper conveying belt 13*a* and the lower conveying belt 13*b*).

A position in the x-direction for cutting the thread-shaped elastic body 7 with the cutting means 18 may be between the nip rollers 171, 172 and the conveying belts 12, 13, between the inner circumferential part and the outer circumferential part of each of the conveying belts 12, 13, or at the outside from the outer circumferential part of each of the conveying belts 12, 13. Further, a variety of known entity capable of cutting the thread-shaped elastic body 7 may be used as the cutting means 18 without specific limitations. For example, it is possible to use a roller cutter which has a cutter roller with a cutting blade arranged at an outer circumferential face along a circumferential direction and an anvil roller for receiving the cutting blade, or the like. Alternatively, cutting may be performed with laser, heat or the like.

Next, description will be performed on a method of manufacturing a stretchable sheet using the abovementioned manufacturing apparatus 11.

First, as illustrated in FIG. 3, the thread-shaped elastic body 7 is continuously unreeled and the unreeled thread-shaped elastic body 7 is introduced to the rotary arm 14 as the elastic body winding means in a stretched state (a supply process).

Specifically, the thread-shaped elastic body 7 is continuously unreeled from the bobbin 70 using the take-off roller 152. In the present embodiment, the bobbin 70 is not rotated. However, the bobbin 70 may be rotated. Then, predetermined tension is applied to the thread-shaped elastic body 7 unreeled from the bobbin 70 by the tension adjusting means 15A. More specifically, tension of the thread-shaped elastic body 7 between the take-off roller 152 and the guide roller 155 is detected by the tension measuring unit 153. The rotation speed of the take-off roller 152 and braking of the tensor 151 are adjusted by the control unit (not illustrated) provided to the manufacturing apparatus 11 based on the detection output from the tension measuring unit 153. Then, tension of the thread-shaped elastic body 7 adjusted to predetermined tension (a predetermined stretching ratio) is provided toward the downstream side from the guide roller 155. Here, braking of the tensor 151 is arranged so that sudden loosening of the thread-shaped elastic body which may occur during unreeling from the bobbin 70 does not influence to a lower process.

The stretching ratio of the thread-shaped elastic body with tension adjusted by the tension adjusting means 15A in a stretchable sheet to be manufactured is preferably in a range of 1.5 to 4.0, more preferably in a range of 1.8 to 3.5, and even more preferably in a range of 2.0 to 3.0.

The stretching ratio can be obtained with the following expression.

Stretching ratio=(Length of stretched thread-shaped elastic body)/(Length of unstretched thread-shaped elastic body(natural length of thread-shaped elastic body))

Then, the thread-shaped elastic body 7 is introduced to the rotary arm 14. At the time of introducing, the thread-shaped elastic body 7 is supplied to the rotary arm 14 while the speed of the thread-shaped elastic body 7 stretched to the predetermined tension (predetermined stretching ratio) by the abovementioned tension adjusting means 15A is adjusted by the speed adjusting means 15B to be equal to or higher than a winding speed of winding the thread-shaped elastic body 7 to the pair of conveying belts 12, 13 with the rotary arm 14 (elastic body winding means).

Here, the "winding speed" denotes a value obtained by dividing a length L (hereinafter, also called an "orbit length L") of the thread-shaped elastic body 7 orbited in one turn at the outer periphery side of the conveying belt 12 (the upper conveying belt 12a and the lower conveying belt 12b) and the outer periphery side of the conveying belt 13 (the upper conveying belt 13a and the lower conveying belt 13b) by a time T required for orbiting in one turn. The speed of the thread-shaped elastic body 7 introduced to the rotary arm 14 (elastic body winding means) and the winding speed of the thread-shaped elastic body 7 are expressed in a unit of [m/sec], for example.

The time T denotes a time from when the thread-shaped elastic body 7 orbiting at the outer periphery side of the conveying belt 12 and the outer periphery side of the conveying belt 13 passes a specific position (e.g., position P1 in FIG. 4) at the periphery of the conveying belt 12 and the conveying belt 13 until when passing the position (e.g., position P2 in FIG. 4) again while moving in the y-direction, as illustrated in FIG. 4. In a case that the elastic body winding means is the rotary arm, the time is equal to the time required for the rotary arm to rotate one turn. Meanwhile, the orbit length L denotes a length L1 being a sum of lengths of sections "a" to "d" in the drawing in consideration of movement of the conveying belts and movement of the thread-shaped elastic body caused thereby, as illustrated in FIG. 4.

Owing to that the speed of the thread-shaped elastic body 7 to be introduced to the rotary arm 14 is adjusted to be equal to or higher than the winding speed by the adjusting means 15B which is arranged at the upstream side of the rotary arm 14 (elastic body winding means), stretchable sheets having constant stretchability can be manufactured stably regardless of the manufacturing speed. Further, as described above, the method for manufacturing a stretchable sheet of the present embodiment can be performed with relatively simple equipment and process.

From a viewpoint of reducing influence of the manufacturing speed, the speed [m/sec] of the thread-shaped elastic body 7 to be introduced to the rotary arm 14 is preferably in a range of 95% to 200% of the winding speed [m/sec], more preferably in a range of 100% to 150%, and even more preferably in a range of 110% to 120%. Here, equality of the speed of the thread-shaped elastic body 7 to be introduced to the rotary arm 14 with the winding speed denotes that the speed of the thread-shaped elastic body 7 to be introduced to the rotary arm 14 is in a range of 95% to 105% of the winding speed. It is preferable that the speed of the thread-shaped elastic body 7 to be introduced to the rotary arm 14 is equal to or higher than the winding speed, especially, is higher than the winding speed.

After the supply process, the thread-shaped elastic body 7 in a stretched state is continuously wound to the pair of conveying belts 12, 13 using the rotary arm 14, and then, the continuously-wound thread-shaped elastic body 7 is conveyed between the pair of belt-shaped sheets 50, 60 using the pair of conveying belts 12, 13 (a conveyance process), as illustrated in FIGS. 2 and 4. More specifically, the thread-shaped elastic body 7 supplied into the rotary arm 14 in a stretched state is introduced into the arm portion 141 from the inlet port 145 and is led out from the outlet port 146 as passing through the shaft portion 142, the connection portion 144, and the orbiting portion 143. The thread-shaped elastic body 7 to be led out from the outlet port 146 is led out while the rotary arm 14 is rotated, so that the thread-shaped elastic body 7 is wound to the outer periphery of the end part at the upstream side of the conveying belt 12 (the upper conveying belt 12a and the lower conveying belt 12b) and the outer periphery side of the end part at the upstream side of the conveying belt 13 (the upper conveying belt 13a and the lower conveying belt 13b). Here, owing to rotational driving of the conveying belt 12 (the upper conveying belt 12a and the lower conveying belt 12b) and the conveying belt 13 (the upper conveying belt 13a and the lower conveying belt 13b), the thread-shaped elastic body 7 is continuously wound like a spiral to the outer periphery side of the conveying belt 12 (the upper conveying belt 12a and the lower conveying belt 12b) and the outer periphery side of the conveying belt 13 (the upper conveying belt 13a and the lower conveying belt 13b). The continuously-wound thread-shaped elastic body 7 is conveyed between the pair of belt-shaped sheets 50, 60 at the downstream side.

Here, the thread-shaped elastic body 7 wound to the pair of conveying belts 12, 13 is not arranged in a direction perpendicular to the y-direction as being stretched in a direction intersecting with the y-direction. To correct the wound thread-shaped elastic body 7 into the direction (x-direction) perpendicular to the y-direction, in a case that the thread-shaped elastic body 7 is wound as illustrated in FIG. 2, for example, the rotation speed of the upper conveying belt 12a is set slower than the rotation speed of the lower conveying belt 12b in the conveying belt 12 and the rotation speed of the lower conveying belt 13b is set slower than the rotation speed of the upper conveying belt 13a in the conveying belt 13. Accordingly, inclination of the thread-shaped elastic body 7 is gradually varied during conveyance in the y-direction and the inclination of the thread-shaped elastic body 7 can be corrected into the direction (x-direction) perpendicular to the y-direction by the time of being conveyed between the pair of belt-shaped sheets 50, 60.

As illustrated in FIG. 2, the belt-shaped sheet 50 is previously folded at both end parts in the x-direction respectively to the outer face side by a folding means (not illustrated) and is supplied between the pair of nip rollers 171, 172 from the upper side of the conveying belt 12 (the upper conveying belt 12a and the lower conveying belt 12b) and the conveying belt 13 (the upper conveying belt 13a and the lower conveying belt 13b). Further, as illustrated in FIG. 2, the belt-shaped sheet 60 is previously folded at both end parts in the x-direction respectively to the outer face side by a folding means (not illustrated) and is supplied between the pair of nip rollers 171, 172 from the lower side of the conveying belt 12 (the upper conveying belt 12a and the lower conveying belt 12b) and the conveying belt 13 (the upper conveying belt 13a and the lower conveying belt 13b). Here, an adhesive is applied to the inner face side(s) of the belt-shaped sheet 50 and/or the belt-shaped sheet 60 before the sheets are supplied between the pair of nip rollers 171, 172. The adhesive may be applied in stripes, spirals, sine-waves or the like, may be sprayed to the entire face, or may be applied in a solid manner.

Subsequently, the thread-shaped elastic body 7 is fixed between the pair of belt-shaped sheets 50, 60 in a stretched state using the nip rollers 171, 172 (an integration process). More specifically, a continuous member having the continuously-wound thread-shaped elastic body 7 arranged between the pair of belt-shaped sheets 50, 60 is supplied between the pair of nip rollers 171, 172 and the thread-shaped elastic body 7 is fixed between the pair of belt-shaped sheets 50, 60 in a stretched state.

Subsequently, the thread-shaped elastic body 7 extended from both end parts in the width direction (x-direction) of the pair of belt-shaped sheets 50, 60 is cut by the above-mentioned cutter 180 (a cutting process).

Subsequently, the folding at both the end parts in the x-direction of the belt-shaped sheets 50, 60 folded to the outer face side are corrected respectively by a folding means (not illustrated) or the like. Thus, it is possible to continuously manufacture a belt-shaped stretchable sheet in which the thread-shaped elastic body 7 is fixed between the pair of belt-shaped sheets 50, 60 in a state of being stretched in the direction intersecting with the y-direction. The manufactured belt-shaped stretchable sheet is intermittently cut along the x-direction with known cutting means (not illustrated). The interval of the discontinuous cutting is the same as a dimension of the waist panel 3 provided to the diaper 1. With the above, it is possible to continuously manufacture the waist panels 3 (stretchable sheets).

As a method of manufacturing the diaper 1 which includes the waist panel 3, a continuous member of the absorbent body 2 is manufactured in a separate process with a known method. The continuous member of the absorbent body 2 includes a continuous member of the topsheet 21, a continuous member of the backsheet 22, a plurality of the absorbent members 23, 23, arranged discontinuously in the conveyance direction (y-direction) between the continuous members of both the sheets 21, 22, a plurality of the elongated elastic members 25 and continuous members of the standing-guard forming sheets 24 arranged at both side parts of the continuous member of the topsheet 21 in the conveyance direction (y-direction).

A pair of the waist panels 3 is arranged for each absorbent member 33 included in the continuous member of the absorbent body 2 as being protruded bilaterally outward in the x-direction while the continuous member of the absorbent body 2 manufactured as described above is conveyed in the conveyance direction (y-direction). Thus, a continuous member of the diaper 1 is manufactured. Here, the conveyance direction (y-direction) of the continuous member of the absorbent body 2 is the same as the conveyance direction (y-direction) when manufacturing the waist panel 3 (stretchable sheet). Therefore, it is not required to rotate the waist panel 3 (stretchable sheet) by 90°. Subsequently, the continuous member is cut into dimensions of each diaper 1 with known cutting means (not illustrated). Thus, the diaper 1 can be manufactured.

Not being limited to the abovementioned embodiment in any way, the method for manufacturing a stretchable sheet of the present invention may be appropriately modified.

For example, although the pair of waist panels 3, 3 is rectangular in FIG. 1, it may be like trapezoids or parallelograms. It is preferable to have a shape to lessen portions to be wasted to the extent possible when forming the pair of waist panels 3, 3 by cutting the stretchable sheet. Further, the inclination of the thread-shaped elastic body 7 is corrected into the direction (x-direction) perpendicular to the y-direction. However, the pair of belt-shaped sheets 50, 60 may be fixed as remaining at angles wound to the conveying belt 12 without being corrected.

Further, the elastic body winding means may adopt a structure which includes a disc having an inlet portion of the thread-shaped elastic body at a rotation axis portion and an arm protruded from the disc to the downstream side in the y-direction and in which the thread-shaped elastic body is wound around the conveying belts 12, 13 with orbiting of the arm around the conveying belts 12, 13, or the like. Further, the feed roller 156 may have a structure to feed a material (thread-shaped elastic body) by sandwiching the material with nip rollers, or the like instead of feeding the material by winding the material as illustrated in FIG. 2.

Further, instead of introducing belt-shaped sheets narrowed by folding back both end parts in the width direction respectively to the outer face side between the pair of nip rollers 170, 171 and fixing the thread-shaped elastic body between the belt-shaped sheets, it is also possible to introduce belt-shaped sheets without both end parts in the width direction folded back and to fix the thread-shaped elastic body between the belt-shaped sheets.

Further, instead of the pair of conveying belts, a conveyer belt as disclosed in WO2005/060910A1 may be adopted as the conveying belt. In this case, only one conveyer belt is required to be used. Further, a thread support member with screw grooves formed disclosed in FIGS. 4 to 6 of JP2002-192641A may be adopted as the thread-conveying longitudinal structure.

In relation to the abovementioned embodiments, the present invention further discloses the following manufacturing methods and absorbent article manufacturing methods.

[1] A method for continuously manufacturing a stretchable sheet with a thread-shaped elastic body fixed between a pair of belt-shaped sheets in a state of being stretched in a direction intersecting with a conveyance direction of the belt-shaped sheets, including a supply process of continuously feeding the thread-shaped elastic body and introducing the fed thread-shaped elastic body to elastic body winding means; a conveyance process of continuously winding the thread-shaped elastic body to a thread-conveying longitudinal structure using the elastic body winding means and conveying the wound thread-shaped elastic body in a longitudinal direction of the thread-conveying longitudinal structure; and an integration process of fixing the conveyed thread-shaped elastic body as sandwiching between the sheets, wherein, in the supply process, the thread-shaped elastic body is introduced to the elastic body winding means while adjusting a speed of the thread-shaped elastic body to be equal to or higher than a winding speed to the thread-conveying longitudinal structure with speed adjusting means which is arranged at the upstream side of the elastic body winding means.

[2] The method according to subject [1], wherein, in the supply process, the thread-shaped elastic body is introduced to the elastic body winding means while adjusting a tensional force thereof to constant tension with tension adjusting means which is arranged at the upstream side of the speed adjusting means and adjusting a speed of the thread-shaped elastic body with the speed adjusting means.

[3] The method according to subject [1] or [2], wherein the thread-conveying longitudinal structure is a pair of conveying belts separated in a direction perpendicular to a longitudinal direction of the thread-conveying longitudinal structure.

[4] The method according to any one of subjects [1] to [3], wherein the speed adjusting means includes a feed roller and a guide roller and adjusts the speed of the thread-shaped elastic body by increasing or decreasing a rotation speed of the feed roller.

[5] The method according to any one of subjects [1] to [4], wherein the thread-shaped elastic body is led out from a bobbin, and a length of a conveyance passage of the thread-shaped elastic body after leaving from the feed roller until being introduced to the elastic body winding means is in a range of 10% to 50%, and more preferably in a range of 10% to 30%, against a total length of the conveyance passage of the thread-shaped elastic body from the bobbin to the elastic body winding means.

[6] The method according to any one of subjects [1] to [5], wherein the tension adjusting means includes a tensor to apply tension to the thread-shaped elastic body with braking, a take-off roller located at the downstream side of the tensor and a tension measuring unit and adjusts tension of the thread-shaped elastic body by increasing or decreasing a rotation speed of the take-off roller based on a detection output from the tension measuring unit.

[7] The method according to any one of subjects [1] to [6], wherein the speed of the thread-shaped elastic body introduced to the elastic body winding means is set to be in a range of 95% to 200%, more preferably in a range of 100% to 150%, and even more preferably in a range of 110% to 120%, of the winding speed against the thread-conveying longitudinal structure.

[8] A method for manufacturing a disposable diaper including a waist panel using a stretchable sheet, wherein the stretchable sheet is manufactured with the method for manufacturing a stretchable sheet according to any one of subjects [1] to [7].

Further, other than the waist panel 3 of the disposable diaper 1, the stretchable sheet manufactured with the manufacturing method of the present invention may be used for a waist portion of a disposable diaper being an open-style type or an underpants type, a waist portion of an underpants type disposable diaper, an underpants type sanitary napkin, disposable underwear, an ear-fit portion of a disposable mask, a cleaning sheet, a bandage, and the like.

EXAMPLES

In the following, the present invention will be described more specifically with examples. Here, the present invention is not limited to the following description in any way.

Example 1

A stretchable sheet with the thread-shaped elastic body 7 fixed between the belt-shaped sheets 50, 60 is manufactured using the stretchable sheet manufacturing apparatus illustrated in FIG. 2. For manufacturing the stretchable sheet, tension of the thread-shaped elastic body 7 unreeled from the bobbin 70 is controlled, by the tension adjusting means 15A including the take-off roller 152, to be constant tension (set to be in a range of 0 to 100 gf (85 gf in Example 1) so that thread rubber tension measured by the tension measuring unit 153 is to be a desired stretch stress of the stretchable sheet). Further, the thread-shaped elastic body 7 is introduced to the rotary arm 14 while the speed thereof is adjusted to be 115% of the winding speed against the conveying belts by the speed adjusting means 15B having the feed roller 156 as a main component. In winding the thread-shaped elastic body with the rotary arm 14, the winding length L1 was 1362 m, the winding time T was 60 seconds, and the winding speed (L1/T) was 22.7 msec (1362 m/min). Further, a conveyance speed of the stretchable sheet (an extraction speed of the stretchable sheet from a space between the rollers 171, 172 as being the same as a circumferential speed of the rollers 171, 172) was 16.8 m/min.

The stretching ratio of the thread-shaped elastic body in the obtained stretchable sheet was measured to be 1.9.

Next, stretchable sheets were manufactured as varying the stretchable sheet conveyance speed to 33.6 m/min, 50.4 m/min, and 67.2 m/min in sequence. Similarly to the abovementioned case, in tension control by the tension adjusting means 15A and introducing speed control by the speed adjusting means 15B, the thread rubber tension measured by the tension measuring unit 153 is set to be in a range of 0 to 100 gf so as to be the desired stretch stress of the stretchable sheet. In the present example, the above was performed to be 85 gf. In every case of the above, the stretching ratio of the thread-shaped elastic body in the obtained stretchable sheet was 1.9.

Example 2

Stretchable sheets were manufactured similarly to Example 1 except for that the speed of the thread-shaped elastic body 7 adjusted by the speed adjusting means 15B was 100% of the winding speed against the conveying belts. The stretching ratios of the thread-shaped elastic body in the obtained stretchable sheets were 2.0, 2.0, and 2.1 in sequence.

Comparative Example 1

Stretchable sheets were manufactured similarly to Example 1 except for that the speed control by the speed adjusting means 15B was not performed as removing the speed adjusting means 15B from the apparatus used in Example 1.

The stretchable sheets were manufactured as varying the circumferential speed of the rollers 171, 172 to 33.6 m/min, 50.4 m/min, and 67.2 m/min in sequence. Similarly to the abovementioned case, in tension control by the tension adjusting means 15A, the thread rubber tension measured by the tension measuring unit 153 is set to be in a range of 0 to 100 gf so as to be the desired stretch stress of the stretchable sheet. The above was performed to be 85 gf also in Comparative Example 1. The stretching ratios of the thread-shaped elastic body in the obtained stretchable sheets were 2.2, 2.4, and 3.0 in sequence.

[Evaluation]

Following is comparison of results of Example 1, Example 2, and Comparative Example 1. Comparative Example 1 indicates a noticeable tendency that the stretching ratio is increased with increase of the sheet conveyance speed. The stretching ratio became 3.0 with the sheet conveyance speed of 67.2 m/min from 1.9 with the sheet conveyance speed of 33.6 m/min. Compared to the above, the increasing tendency of the stretching ratio is drastically reduced in Example 2. The stretching ratio resulted in 2.1 with the sheet conveyance speed of 67.2 m/min from 1.8 with the sheet conveyance speed of 33.6 m/min. In contrast, in Example 1, the stretching ratio stayed constant as being 1.9 even though the sheet conveyance speed was increased. The above proves that the present invention enables stretchable sheets having stable stretchability to be effectively manufactured even with an increased manufacturing speed.

INDUSTRIAL APPLICABILITY

The method for manufacturing a stretchable sheet of the present invention provides a stretchable sheet manufacturing method capable of stably manufacturing stretchable sheets having constant stretchability regardless of a manufacturing speed, wherein, in the stretchable sheet, a thread-shaped elastic body is fixed between a pair of belt-shaped sheets in a state of being stretched in a direction intersecting with a conveyance direction of the belt-shaped sheets.

The invention claimed is:

1. A method for continuously manufacturing a stretchable sheet with a thread-shaped elastic body fixed between a pair of belt-shaped sheets in a state of being stretched in a direction intersecting with a conveyance direction of the belt-shaped sheets, comprising:
   a supply process of continuously feeding the thread-shaped elastic body and introducing the fed thread-shaped elastic body to elastic body winding means, wherein, in the supply process, the thread-shaped elastic body is introduced to the elastic body winding means while adjusting a tensional force thereof to constant tension with tension adjusting means which is arranged at the upstream side of the speed adjusting means and adjusting a speed of the thread-shaped elastic body with the speed adjusting means;
   a conveyance process of continuously winding the thread-shaped elastic body to a thread-conveying longitudinal structure using the elastic body winding means and conveying the wound thread-shaped elastic body in a longitudinal direction of the thread-conveying longitudinal structure; and
   an integration process of fixing the conveyed thread-shaped elastic body as sandwiching between the sheets,
   wherein, the elastic body winding means have a servomotor, and adjusts a winding speed of the thread-shaped elastic body by controlling a rotation speed of the servomotor, and
   in the supply process, a tensional force of the thread-shaped elastic body is adjusted to constant tension with tension adjusting means, and the thread-shaped elastic body is introduced to the elastic body winding means while adjusting a speed of the thread-shaped elastic body to be higher than the winding speed to the thread-conveying longitudinal structure with speed adjusting means which is arranged at the upstream side of the elastic body winding means and is located at the downstream side of the tension adjusting means, the thread-shaped elastic body being wound to the thread-conveying longitudinal structure by the rotation of the elastic body winding means,
   wherein the speed adjusting means comprises a feed roller arranged immediately before the elastic body winding means in a conveyance passage of the thread-shaped elastic body, guide rollers and a servomotor for rotating the feed roller, the feed roller being disposed between the guide rollers, so that the thread-shaped elastic body is continuously supplied to the elastic body winding means through the feed roller and the guide rollers and the speed of the thread-shaped elastic body is adjusted by increasing or decreasing a rotation speed of the feed roller by the servomotor for rotating the feed roller,
   wherein the thread-shaped elastic body is led out from a bobbin, and a length of a conveyance passage of the thread-shaped elastic body after leaving from the feed roller until being introduced to the elastic body winding means is in a range of 10% to 50% against a total length of the conveyance passage of the thread-shaped elastic body from the bobbin to the elastic body winding means,
   wherein, in the supply process, a tensional force of the thread-shaped elastic body is adjusted with tension adjusting means which is arranged at the upstream side of the speed adjusting means, and the tension adjusting means includes a tensor to apply tension to the thread-shaped elastic body with braking, a take-off roller located at the downstream side of the tensor and a tension measuring unit and adjusts tension of the thread-shaped elastic body by increasing or decreasing a rotation speed of the take-off roller based on a detection output from the tension measuring unit,
   wherein the speed of the thread-shaped elastic body introduced to the elastic body winding means is set to be in a range of 110% to 120% of the winding speed to the thread-conveying longitudinal structure, and
   wherein the stretching ratio of the thread-shaped elastic body with tension adjusted by the tension adjusting means in a stretchable sheet to be manufactured is in a range of 1.5 to 4.0.

2. The method according to claim 1, wherein the thread-conveying longitudinal structure is a pair of conveying belts separated in a direction perpendicular to a longitudinal direction of the thread-conveying longitudinal structure.

3. The method according to claim 1, wherein, in the integration process, the thread-shaped elastic body is fixed between the pair of belt-shaped sheets using a pair of the nip rollers, and an adhesive is applied to the inner face side of the belt-shaped sheet before the belt-shaped sheets are supplied between the pair of nip rollers.

\* \* \* \* \*